United States Patent [19]

Ziegler

[11] 4,120,302
[45] Oct. 17, 1978

[54] DISPOSABLE PADS FOR SURGICAL INSTRUMENTS

[75] Inventor: John S. Ziegler, Arlington Heights, Ill.

[73] Assignee: American Hospital Supply Corporation, Evanston, Ill.

[21] Appl. No.: 730,961

[22] Filed: Oct. 8, 1976

[51] Int. Cl.² ............................................. A61B 17/28
[52] U.S. Cl. ................................. 128/322; 15/250.35; 15/250.36; 15/250.42; 128/325; 128/346
[58] Field of Search ................. 128/321, 322, 346, 20, 128/325; 81/421–424; 15/210 A, 250.35, 250.36, 250.42

[56] References Cited

U.S. PATENT DOCUMENTS

| | | | |
|---|---|---|---|
| 2,307,377 | 1/1943 | Riccardi | 128/346 |
| 2,723,666 | 11/1955 | Greenberg | 128/321 |
| 2,743,726 | 5/1956 | Grieshaber | 128/322 UX |
| 2,766,649 | 10/1956 | Labry | 81/423 X |
| 3,503,396 | 3/1970 | Pierie et al. | 128/322 |
| 3,503,397 | 3/1970 | Fogarty et al. | 128/322 |
| 3,503,398 | 3/1970 | Fogarty et al. | 128/346 |
| 3,515,139 | 6/1970 | Mallina | 128/322 |
| 3,779,248 | 12/1973 | Karman | 128/321 |

Primary Examiner—Robert W. Michell
Assistant Examiner—Michael H. Thaler
Attorney, Agent, or Firm—Tilton, Fallon, Lungmus & Chestnut

[57] ABSTRACT

A disposable pad for use with a surgical instrument having a supporting element. The pad includes a flexible elongated member having a channel therein for slidably receiving the supporting element. A stop member limits longitudinal insertion of the supporting element into the channel, a retention member prevents lateral movement of the supporting element out of the channel, and a latching member secures the supporting element against longitudinal displacement from the channel. The latching member is normally disposed in a latching position but is shiftable into a releasing position as the elongated member is flexed to remove the pad. The supporting element of the surgical instrument can hold an artery or vein or other body tissue without damage when using the disposable pad.

13 Claims, 13 Drawing Figures

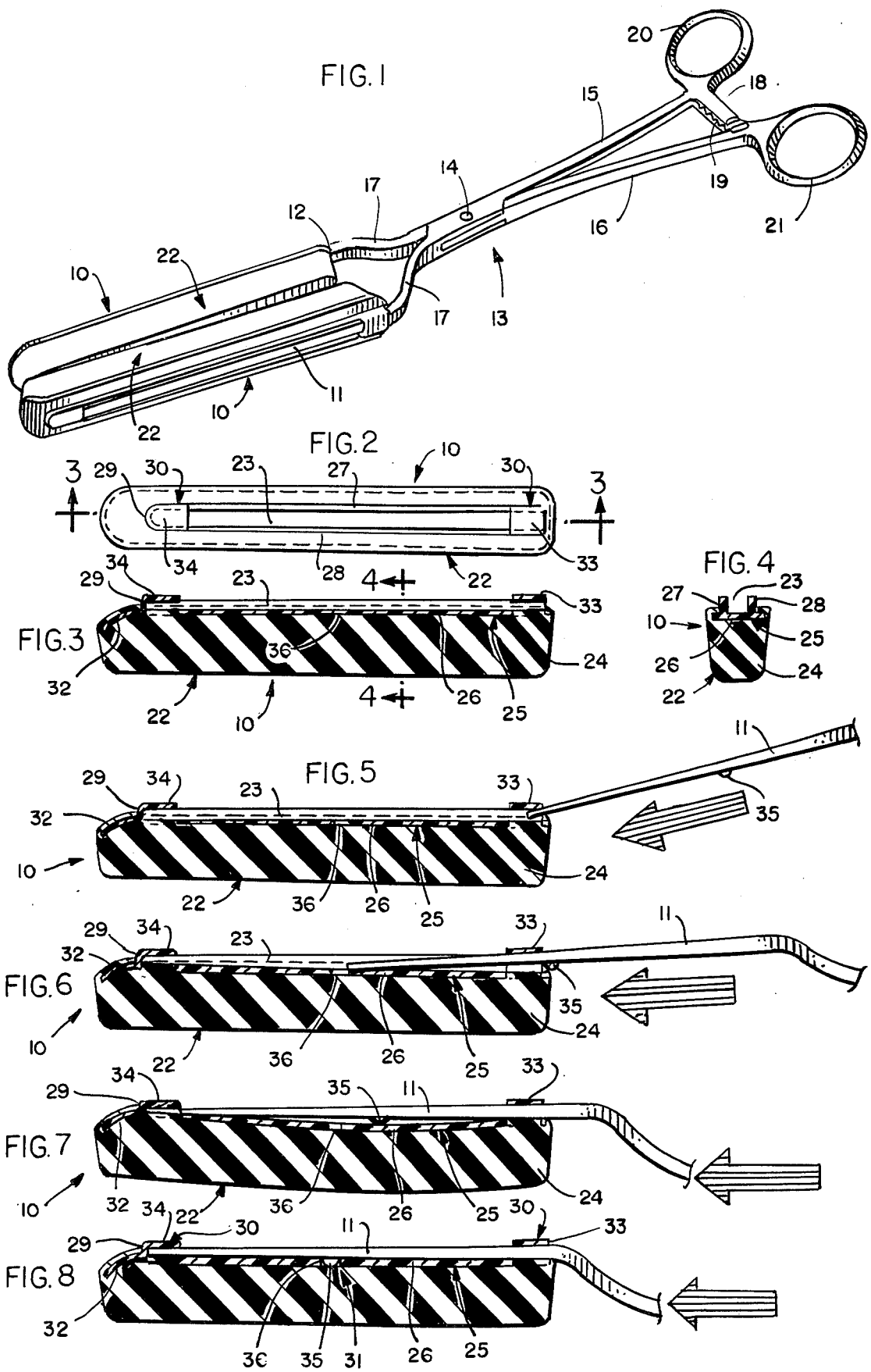

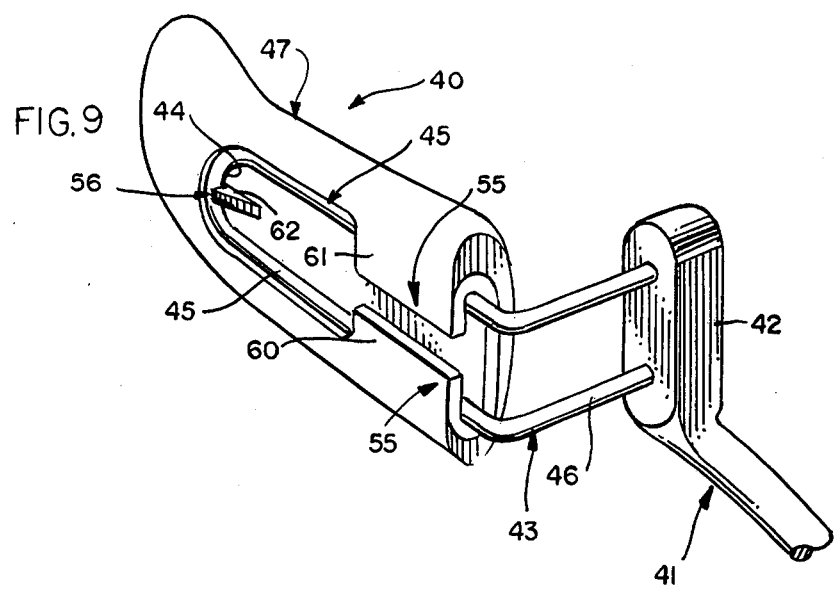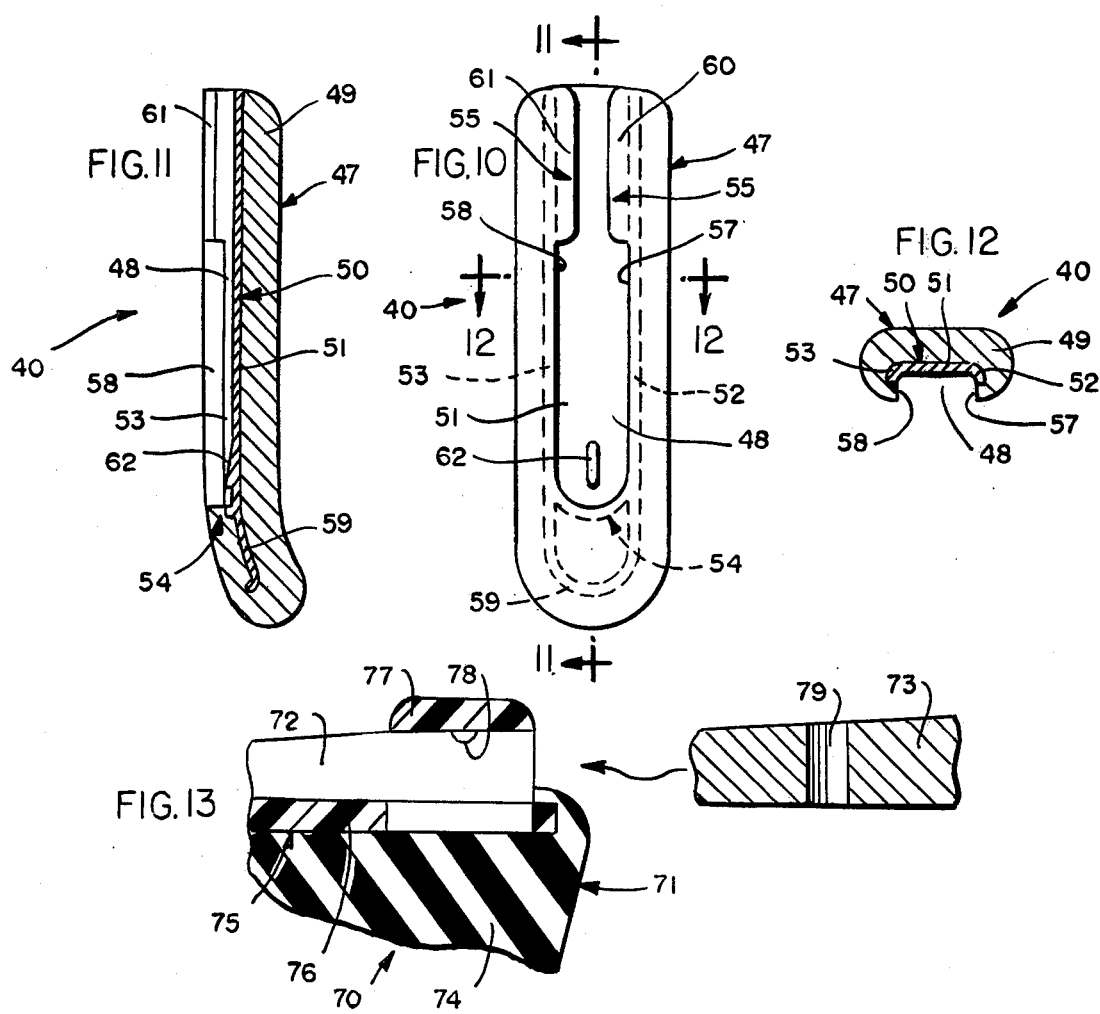

DISPOSABLE PADS FOR SURGICAL INSTRUMENTS

BACKGROUND

This invention relates to a disposable pad for use with a surgical instrument having a supporting element and more particularly to a disposable pad of the type described for holding an artery or vein or other body tissue without damage.

Disposable pads for use with surgical instruments such as clamps and the advantages to be derived therefrom have previously been disclosed in commonly-owned U.S. Pat. Nos. 3,503,396; 3,503,397; and 3,503,398. A pad typically includes a soft elongated member having some means for attaching the member to each jaw of the clamp. The elongated member preferably distributes the clamping force uniformly over the surface being held. The attachment means must therefore be sufficient to support the member securely in place on the jaw of the clamp during use to prevent slippage while at the same time facilitating easy removal of the member after use for disposal. When such means for attaching the soft elongated member to the jaw of the clamp are subjected to various external forces, however, the disposable pad can become disoriented or disengaged possibly causing damage to the artery or vein or other body tissue being held by the clamp.

While the prior art has dealt with the problems associated with temporarily attaching a disposable pad to a surgical instrument and later removing the pad for disposal with varying degrees of success, the present invention represents an improvement over all such prior art constructions.

SUMMARY

The present invention is directed to a disposable pad for use with a surgical instrument having a supporting element. The pad includes a flexible elongated member having a channel therein for slidably receiving the supporting element. Stop means limits longitudinal insertion of the supporting element into the channel, retention means prevents lateral movement of the supporting element out of the channel, and latching means secures the supporting element against longitudinal displacement from the channel. The latching means is normally disposed in a latching position but is shiftable into a releasing position as the elongated member is flexed to bow away from the supporting element.

When the disposable pad is used with a surgical clamp having a pair of elongated jaws which are operatively associated for movement into and out of gripping relation, the flexible elongated member again slidably receives one of the jaws within the channel. Stop means limits longitudinal insertion of the jaw into the channel, retention means prevents lateral movement of the jaw out of the channel, and latching means secures the jaw against longitudinal displacement from the channel. The latching means is again normally disposed in a latching position but is shiftable into a releasing position as the elongated member is flexed to bow away from the jaw.

The latching means preferably includes operatively associated male and female elements. The retention means can advantageously be defined by at least one bridge member spanning the sides of the channel near its proximal end and preferably a second bridge member spanning the sides of the channel near its distal end. The stop means preferably includes an end wall member joining the bottom and sides of the channel as well as the second bridge member near its distal end.

When the removable pad is used with a retractor having at least one arm carrying a hook, the flexible elongated member again slidably receives the hook within the channel. Stop means limits longitudinal insertion of the spring hook into the channel, retention means prevents lateral movement of the hook out of the channel, and latching means secures the hook against longitudinal displacement from the channel. The latching means is again normally disposed in a latching position but is shiftable into a releasing position as the elongated member is flexed to bow away from the hook.

The latching means preferably includes operatively associated male and female elements wherein the male element is a generally wedge-shaped tooth or projection and the female element is a loop. The retention means can advantageously be defined by at least one tab member extending inwardly from one side of the channel near its proximal end and preferably a second tab member extending inwardly from the other side of the channel toward the first tab member also near its proximal end. The stop means preferably includes an end wall member joining the bottom and sides of the channel near its distal end.

The present invention therefore retains the advantages inherent in disposable pads while at the same time providing an improved construction that eliminates the problems associated with such pads in the past. It is therefore an object of the present invention to provide a disposable pad for use with a surgical instrument having a supporting element, that effectively precludes damage to arteries, veins, or other body tissues caused by dislocation of the pad during use, wherein the pad is easily attached and removed from the instrument before and after use. The provision of the disposable pad and the realization of the advantages to be derived therefrom constitute additional important objects of the present invention with still other objects being appreciated from the details of construction and operation set forth in the accompanying specifications, claims and drawings.

DRAWINGS

The invention is described in conjunction with the accompanying drawings in which:

FIG. 1 is a perspective view of a surgical clamp equipped with disposable pads in accordance with the present invention;

FIG. 2 is a plan view of one of the disposable pads of FIG. 1 adapted for use with a surgical clamp;

FIG. 3 is a cross-sectional view of the disposable pad of FIG. 2 taken on the line 3—3;

FIG. 4 is a cross-sectional view of the disposable pad of FIG. 3 taken on the line 4—4;

FIG. 5 is a cross-sectional view of one of the disposable pads of FIG. 1 adapted for use with a surgical clamp illustrating a jaw of the clamp being inserted into a channel in the pad;

FIG. 6 is a cross-sectional view of the disposable pad similar to FIG. 5 illustrating the jaw of the clamp being inserted further into the channel in the pad;

FIG. 7 is a cross-sectional view of the disposable pad similar to FIG. 6 illustrating the jaw of the clamp being inserted still further into the channel in the pad;

FIG. 8 is a cross-sectional view of the disposable pad similar to FIG. 7 illustrating the jaw of the clamp fully inserted into the channel in the pad;

FIG. 9 is a fragmentary perspective view of a surgical retractor equipped with a disposable pad in accordance with the present invention;

FIG. 10 is a plan view of the disposable pad of FIG. 9 adapted for use with a surgical retractor;

FIG. 11 is a cross-sectional view of the disposable pad of FIG. 10 taken on the line 11—11;

FIG. 12 is a cross-sectional view of the disposable pad of FIG. 10 taken on the line 12—12; and FIG. 13 is a fragmentary cross-sectional view of another form of a disposable pad adapted for use with a surgical clamp illustrating a jaw of the clamp being inserted into a channel in the pad.

DESCRIPTION

In the illustration given and with reference first to FIG. 1, the numeral 10 designates generally a pair of disposable pads in accordance with the present invention. The pads 10 are illustrated in position for use on a pair of supporting elements or jaws 11 and 12 of a surgical clamp 13 which are hinged together as at 14 for movement toward and away from each other. The jaw 11 is integral with the handle portion 15 and the jaw 12 is integral with the handle portion 16 to provide scissors action for opening and closing the jaws. The jaws 11 and 12 may be bent as at 17 to a considerable angle relative to the pivotal and handle portions to accommodate the thickness of the pads 10. The handles 15 and 16 have lugs 18 and 19 equipped with interengaging ratchet teeth to lock the jaws in closed or partially closed positions. The lugs 18 and 19 are provided remote from the hinge or pivot point 14 adjacent the point where the handles 15 and 16 terminate in finger rings 20 and 21. While the foregoing constitutes a somewhat detailed description of the surgical clamp 13, it has been provided merely to establish an environment for more fully understanding the disposable pads 10 which are actually well suited for use with any surgical instrument having a supporting element.

The disposable pad 10 includes a flexible elongated member 22 having a channel 23 therein (as shown in FIG. 4) for slidably receiving the jaw 11 or 12 of the surgical clamp 13. The member 22 preferably includes two integrated parts with one of the parts being a cushion 24 and the other of the parts being a member 25 defining the channel 23. The channel-defining member 25 includes a bottom portion 26 supporting two generally parallel upstanding side portions 27 and 28. The side portions 27 and 28 and the bottom portion 26 are so arranged as to provide the channel 23 with a generally U-shaped cross-section.

The member 22 has a channel 23 as discussed hereinabove which slidably receives the jaw 11 or 12 of the surgical clamp 13. Stop means 29 limits longitudinal insertion of the jaw 11 or 12 into the channel 23, retention means 30 prevents lateral movement of the jaw 11 or 12 out of the channel 23, and latching means 31 secures the jaw 11 or 12 against longitudinal displacement from the channel 23. The latching means 31 is normally disposed in a latching position (as shown in FIG. 8) but is shiftable into a releasing position (as shown in FIG. 7) as the member 22 is flexed to bow away from the jaw 11 or 12 intermediate its ends.

The stop means 29 is preferably an end wall member (as shown in FIGS. 2 and 8) joining the bottom portion 26 and the side portions 27 and 28 near the distal end of the channel-defining member 25. The end wall member 29 may be formed integrally with a downwardly-curving extension 32, the extension 32 not only reinforcing the end wall 29 but also serving to control or limit deformation of that portion of the cushion 24 extending beyond the end of the supporting element or jaw 11 or 12.

The retention means 30 is preferably a bridge member 33 (as shown in FIGS. 2 and 8) spanning the side portions 27 and 28 near the proximal end of the channel-defining member 25 with a second bridge member 34 advantageously being provided near the distal end. The second bridge member 34 joins the upper end of the end wall member 29 as well as spanning the side portions 27 and 28 of the channel-defining member 25. When the jaw 11 or 12 has been longitudinally inserted into the channel 23 with the tip of the jaw in contact with the end wall member 29, the bridge members 33 and 34 prevent lateral movement of the jaw 11 or 12 out of the channel 23.

The latching means 31 (as shown in FIG. 8) includes operatively associated male and female elements. The male element is preferably a pin 35 provided intermediate the ends of the inner surface of the jaw 11 with the female element being a hole 36 (as shown in FIG. 7) provided intermediate the ends of the bottom portion 26 of the channel-defining member 25. When the pin 35 is disposed within the hole 36, the latching means 31 secures the jaw 11 against longitudinal displacement from the channel 23.

Referring to FIGS. 5 through 8, the means for attaching the disposable pad 10 to the jaw 11 of the surgical clamp 13 can be more fully appreciated. The tip of the jaw 11, which is narrower and thinner than the portion of the jaw 11 adjacent the bend as at 17, is inserted into the channel 23 under the bridge member 33 (as shown in FIG. 5) and advanced until the pin 35 on the inner surface of the jaw 11 is adjacent the bridge member 33 at the proximal end of the channel 23 (as shown in FIG. 6). The jaw 11 can easily be inserted to this point because its gradually increasing taper still results in a width and thickness that is less than the width and height of the channel 23 adjacent the bridge member 33. The combined thickness of the jaw 11 and the pin 35 is slightly less than the height of the channel 23 resulting in some clearance as the portion of the jaw 11 provided with the pin 35 passes under the bridge member 33.

After the portion of the jaw 11 provided with the pin 35 has passed completely under the bridge member 33, the jaw 11 is inserted further into the channel 23 until the tip of the jaw 11 approaches the second bridge member 34. The jaw 11 can again easily be inserted to this point because its gradually increasing taper still results in a width and thickness that is less than the width and height of the channel 23 adjacent the bridge member 33. The tip of the jaw 11 is then forced downwardly into contact with the bottom portion 26 of the channel-defining member 25 (as shown in FIG. 7) with the pin 35 acting as a pivot point causing the member 22 to bow away from the jaw 11 intermediate its ends.

After forcing the tip of the jaw 11 downwardly into contact with the bottom portion 26 of the channel-defining member 25, the jaw 11 is inserted still further into the channel 23 under the bridge member 34 until the tip of the jaw 11 is in engagement with the end wall member 29 (as shown in FIG. 8). The jaw 11 will be fully inserted at this point with the pin 35 dropping into the hole 36 as the member 22 resumes its normal shape. Since the width and height of the channel 23 under the bridge member 34 is generally the same as the width and thickness of the tip of the jaw 11 and the width and height of the channel 23 under the bridge member 33 is generally the same as the width and thickness of the jaw 11 adjacent the bend as at 17, the jaw 11 is snuggly held in position within the channel 23 by the end wall member 29, the bridge members 33 and 34 and the pin 35 disposed in a latching position within the hole 36.

When it is later desired to remove the jaw 11 from the channel 23, the reverse of the above procedure can be followed. The member 22 is flexed (as shown in FIG. 7) to bow away from the jaw 11 intermediate its ends sufficiently to disengage the pin 35 from the hole 36. The jaw 11 is then withdrawn from the channel 23.

With the above construction, a quick, effective and reliable means for attaching a disposable pad 10 to the supporting element of a surgical instrument is provided. Stop means 29 limits longitudinal insertion of the element into the channel 23, retention means 30 prevents lateral movement of the element out of the channel, and latching means 31 secures the element against longitudinal displacement from the channel 23. The latching means 31 is normally disposed in a latching position but is shiftable into a releasing position as the elongated member 22 is flexed.

In another form of the invention, a disposable pad 40 (as shown in FIG. 9) is provided for use with a surgical retractor 41 having a pair of arms 42 (only one being shown) each of which carries a hook or blade 43. Each hook 43 is generally U-shaped in configuration being equipped with a loop portion 44 and legs 45 extending therefrom along the same general plane. The legs 45 terminate in free end portions 46 which project outwardly from the plane of the legs 45 to be secured within the arm 42. The hooks 43 are formed of a strong and relatively rigid material such as stainless steel. Further details of typical retractor construction may be obtained from commonly-owned U.S. Pat. No. 2,850,008, it being understood that a retractor is disclosed herein to establish an environment for more fully understanding the disposable pads 40 which are again actually well suited for use with any surgical instrument having a supporting element.

The disposable pad 40 includes a flexible elongated member 47 having a channel 48 therein (as shown in FIG. 12) for slidably receiving the support hook 43 of the surgical retractor 41. The member 47 preferably includes two integrated parts with one of the parts being a cushion 49 and the other of the parts being a member 50 defining the channel 48. The channel-defining member 50 includes a bottom portion 51 supporting two upstanding side portions 52 and 53. The side portions 52 and 53 and the bottom portion 51 are arranged to provide the channel 48 with a generally U-shaped cross-section. The side portions 52 and 53 are formed (as shown in FIG. 12) so that in production the channel-defining member 50 can be placed into a mold cavity and the cushion 49 can be formed in place about the channel-defining member 50 by using a plastic foam that completely encases the upper ends of the side portions 52 and 53.

The member 47 has a channel 48 as discussed hereinabove which slidably receives the hook 43 of the surgical retractor 41. Stop means 54 limits longitudinal insertion of the hook 43 into the channel 48, retention means 55 prevents lateral movement of the hook 43 out of the channel 48, and latching means 56 secures the hook 43 against longitudinal displacement from the channel 48. The latching means 56 is normally disposed in a latching position but is shiftable into a releasing position as the member 47 is flexed to bow away from the hook 43 near its distal end.

The stop means 54 is preferably an end wall member (as shown in FIGS. 10 and 11) joining the bottom portion 51 and the side portions 52 and 53 near the distal end of the channel-defining member 50. The side portions 57 and 58 of the cushion 49 which may extend upwardly beyond the side portions 52 and 53 of the channel-defining member 50 (as shown in FIG. 12) may also join near the distal end of the channel-defining member 50 to further define the end wall member of the stop means 54. The end wall member 54 is curved to conform to the loop portion 44 of the hook 43 and terminates in a downardly curving extension 59 of the channel-defining member 50 which is also embedded within the plastic foam of the cushion 49.

The retention means 55 is preferably a tab member 60 (as shown in FIG. 10) extending inwardly from one side near the proximal end of the member 47 with a second tab member 61 also advantageously being provided. The second tab member 61 extends inwardly from the other side near the proximal end of the member 47. When the hook 43 has been longitudinally inserted into the channel 48 with the loop portion 44 in contact with the end wall member 54, the tab members 60 and 61 prevent lateral removal of the hook 43 from the channel 48.

The latching means 56 (as shown in FIG. 9) includes operatively associated male and female elements. The male element is preferably a projection or wedge-shaped tooth 62 provided near the distal end of the bottom portion 51 of the channel-defining member 50 and the female element is defined by the loop portion 44 of the hook 43. When the wedge-shaped tooth 62 is disposed within the loop portion 44, the latching means 56 secures the hook 43 against longitudinal displacement from the channel 48.

Referring to FIG. 9, the means for attaching the disposable pad 40 to the support hook 43 of the surgical retractor 41 can be more fully appreciated. The hook 43 is inserted into the channel 48 under the tab members 60 and 61 and advanced until the loop portion 44 is adjacent the wedge-shaped tooth 62 near the distal end of the channel 48. The hook 43 can easily be inserted to this point because the legs 45 are spaced apart a distance the same as or slightly less than the distance between the side portions 52 and 53 of the channel-defining member 50 and the side portions 57 and 58 of the cushion 49 which serves as guides with nothing to obstruct inward movement. However, the loop portion of the hook 43 eventually contacts the wedge-shaped tooth 62 which offers some resistance to further insertion of the hook 43 into the channel-defining member 50.

After the loop portion 44 has made contact with the wedge-shaped tooth 62, the hook 43 is inserted further into the channel 48 by urging it inwardly which forces it to ride upwardly on the wedge-shaped tooth 62 causing the member 47 to bow away from the hook 43 near its distal end. The loop portion 41 will continue to exert a wedging action against the tooth 62 until it clears the tooth 62 and engages the end wall member 54 at which point the tooth 62 will snap into the loop portion 44 as the member 47 resumes its normal position. Since the loop portion 44 is confined within the channel 48 between the end wall member 54 and the wedge-shaped tooth 62 and the legs 45 are confined within the channel 48 by the tab members 60 and 61, the hook 43 is snuggly held in position within the channel-defining member 50.

When it is later desired to remove the hook 43 from the channel 48, the reverse of the above procedure can be followed. The member 47 is flexed to bow away from the hook 43 near its distal end sufficiently to disengage the wedge-shaped tooth 62 from the loop portion 44. The hook 43 is then withdrawn from the channel 48 until the loop portion 44 clears the upper extreme of the wedge-shaped tooth 62 and is further withdrawn causing the loop portion 44 to slide downwardly on the wedge-shaped tooth 62 and outwardly on the bottom portion 51 of the channel-defining member 50. The relative sliding movement between the channel 48 and the hook 43 is continued until the hook 43 has been fully withdrawn from the channel 48 for disposal of the pad 40.

With this alternative construction, another quick, effective and reliable means for attaching a disposable pad 40 to the supporting element of a surgical instrument is provided. Stop means 54 limits longitudinal insertion of the element into the channel 48, retention means 55 prevents lateral movement of the element out of the channel and latching means 56 secures the element against longitudinal displacement from the channel 48. The latching means 56 is normally disposed in a latching position but is shiftable into a releasing position as the elongated member 47 is flexed.

In still another form of the invention useful with surgical clamps such as the one illustrated in FIGS. 1 through 8, the latching means (as shown in FIG. 13) includes operatively associated male and female elements but in a somewhat different configuration. The latching means of this embodiment is illustrated with a disposable pad 70 that includes a flexible elongated member 71 having a channel 72 therein for slidably receiving a jaw 73 of a surgical clamp. It should be noted that the flexible elongated member 71 (partially shown) and the jaw 73 (partially shown) are essentially identical to the flexible elongated member 22 and the jaw 11 (as shown in FIGS. 1 through 8) with the exception of the latching means. The flexible elongated member 71 preferably includes two integrated parts with one of the parts being a cushion 74 and the other of the parts being a member 75 defining the channel 72. The channel-defining member 75 has a bottom portion 76 supporting two generally parallel inwardly set upstanding side portions (as shown in FIG. 4) and a bridge member 77 spans the side portions near the proximal end of the channel-defining member 75 to prevent lateral movement of the jaw 73 out of the channel 72. With respect to other structural details of the form of the invention illustrated in FIG. 13, apart from the latching means to be described hereinafter, reference may be made to the description of the embodiment illustrated in FIGS. 1 through 8 hereinabove.

The latching means includes operatively associated male and female elements normally disposed in a latching position but shiftable into a releasing position as the bridge member portion 77 of the flexible elongated member 71 is flexed to bow away from the jaw 73 near its proximal end. The male element is preferably a pin or nub 78 provided on the undersurface of the bridge member portion 77 with the female element being a hole 79 provided in the jaw 73 near its proximal end. The hole 79 is positioned so that the pin or nub 78 will engage it when the jaw 73 is fully inserted into the channel 72. When the pin or nub 78 is disposed within the hole 79, the latching means secures the jaw 73 against longitudinal displacement from the channel 72.

Referring to FIG. 13, the means for attaching the disposable pad 70 to the jaw 73 of the surgical clamp can be more fully appreciated. The tip of the jaw 73 (not shown) narrower and thinner than the portion of the jaw 73 adjacent the bend (not shown), is inserted into the chhanel 72 under the bridge member portion 77 and advanced until the hole 79 in the jaw 73 engages the pin 78. The thickness of the jaw 73 in the region of the hole 79 is about the same as the height of the channel 72, but the height of the channel 72 under the pin or nub 78 is significantly less than the thickness of the jaw 73 as the jaw 73 passes further under the bridge member portion 77. Therefore, the bridge member portion 77 is gradually forced upward by the taper of the jaw 73 until it snaps back into its original shape when the pin 78 engages the hole 79.

As the jaw 73 is inserted into the channel 72, the tip of the jaw 73 approaches a second bridge member (not shown). The tip of the jaw 73 is then forced downwardly into contact with the bottom portion 76 of the channel-defining member 75 and the jaw 73 is then inserted still further into the channel 72 under the second bridge member until the tip of the jaw 73 is in engagement with the end wall member (not shown). The jaw 73 will be fully inserted at this point with the pin 78 snapping into the hole 79 as described above. Since the width and height of the channel 72 under the second bridge member is generally the same as the width and thickness of the tip of the jaw 73 and the width and height of the channel 72 under the bridge member 77 (exclusive of the pin or nub 79) is generally the same as the width and thickness of the jaw 73 adjacent the hole 79, the jaw 73 is snuggly held in position within the channel 72 by the end wall member, the bridge members, and the pin or nub 78 disposed in a latching position within the hole 79.

When it is later desired to remove the jaw 73 from the channel 72, the reverse of the above procedure can be followed. The jaw 73 is pulled longitudinally from the channel 72 causing the bridge member portion 77 of the flexible elongated member 71 to bow away from the jaw 73 near the proximal end of the member 71 as the pin or nub 78 becomes disengaged from the hole 79. A slight taper on the pin 78 causes it to ride up out of the hole 79 with the bridge member portion 77 of the flexible elongated member 71 flexing to bring this about or the pin or nub 78 may simply be sheared off by the pulling action. The jaw is then fully withdrawn from the channel 72 for disposal of the pad 70.

With this additional alternative construction, still another quick, effective and reliable means for attaching a disposable pad 70 to the supporting element of a surgical instrument is provided. Stop means limits longitudinal insertion of the element into the channel 72, retention means prevents lateral movement of the element out of the channel 72, and latching means secures the element against longitudinal displacement from the channel 72. The latching means 78 is normally disposed in a latching position but is shiftable into a releasing position as the bridge member portion 77 of the flexible elongated member 71 is flexed.

The present invention therefore provides pads useful with surgical instruments having a relatively rigid supporting element which are removable and disposable in all of their forms providing a resilient atraumatic cushion for contacting an artery, vein or other body tissue. The pads can advantageously be formed of two integrated parts with one of the parts being a channel-defining member formed of resilient plastic and the other of the parts being a cushion formed of a liquid absorbent polyurethane foam. However, they need not be absorbent nor must they be formed of plastic much less a resilient plastic and their surfaces can have teeth, ridges, or other contours depending upon the particular surgical use to which they will be applied. The pads can be formed of foam rubber, solid rubber, gauze or textiles, semi-rigid plastics, fluid-filled plastics or other materials as long as they are capable of flexing and it is also possible to form them of a single material throughout especially in the event that a relatively hard construction is desired. With the present invention, a unique latching action occurs as the relatively rigid supporting element of the surgical instrument is fully inserted into the channel in the disposable pad to secure the pad against inadvertent longitudinal displacement or detachment.

The unique latching action of the disposable pads is achieved by flexing the pad itself with pairs of male and female elements comprising the latching elements. In the first embodiment (FIGS. 1 through 8), the male element is provided by a jaw of a surgical clamp whereas the female element is provided by the pad. In the second embodiment (FIGS. 9 through 12), the male element is provided by the pad whereas the female element is provided by a hook of a retractor. In the third embodiment (FIG. 13), the male element is again provided by the pad whereas the female element is provided by a jaw of a surgical clamp. With all three embodiments, the disposable pads which are, in most instances, even more firmly secured in a latching position during use must flex to engage and disengage the pairs of male and female elements comprising the latching elements.

The disposable pads of the present invention may be attached to surgical instruments for the purpose of cushioning, fluid absorption, improved traction, or controlled pressure distribution over a desired contact area. Since these pads are commonly supplied as sterile disposables, it is important to have a quick, simple, reliable way of attaching them to the permanent part of the instrument and subsequently removing them for disposal. Several ways of achieving this objective have been developed and used in the past although none of them have been completely effective prior to the present invention which achieves these objectives in a simple yet effective disposable pad having adaptability for use with numerous surgical instruments.

While in the foregoing specification a detailed description of the invention has been set forth for purposes of illustration, variation of the details herein given may be made by those skilled in the art without departing from the spirit and scope of the invention.

I claim:

1. A disposable pad for use with a surgical instrument comprising a resilient flexible elongated member of generally U-shaped cross sectional configuration having proximal and distal ends and having an open-sided channel therein for slidably receiving a supporting element of said instrument, stop means provided by said pad adjacent said distal end for limiting the longitudinal insertion of said element into said channel from the proximal end of said member, retention means for preventing transverse movement of said element out of said channel, said retention means being located adjacent the proximal end of said flexible elongated member and completely bridging said channel, and latching means provided by said member for securing said element against longitudinal displacement from said channel, said latching means normally being disposed in a latching position but being shiftable into a releasing position as said elongated member is flexed.

2. The disposable pad of claim 1 in which said flexible elongated member includes two integrated parts with one of said parts being a resilient plastic foam cushion and the other of said parts being a flexible member defining said channel.

3. The disposable pad of claim 2 in which said channel-defining member is formed of a resilient plastic.

4. The disposable pad of claim 1 in which said retention means includes a bridge member completely spanning said channel adjacent the proximal end of said flexible member.

5. The disposable pad of claim 1 in which second retention means is provided by said pad and includes a second bridge member completely spanning said channel adjacent the distal end of said flexible member.

6. The disposable pad of claim 1 in which said stop means includes an end wall member joining the bottom and sides of said channel-defining member near its distal end.

7. The disposable pad of claim 5 in which said end wall member and said bridge members are integral with said channel-defining member.

8. The disposable pad of claim 1 in which said latching means includes one element of a pair of operatively associated male and female elements, the other of said elements being provided by said surgical instrument.

9. The disposable pad of claim 8 in which said one element is provided intermediate the ends of said channel-defining member and within said channel.

10. The disposable pad of claim 9 in which said one element is a pin projecting from said member within said channel at an intermediate point spaced between said proximal and distal ends.

11. A disposable pad and surgical clamp combination, said surgical clamp having a pair of elongated jaws operatively associated for movement into and out of gripping relation, said pad comprising a resilient flexible elongated member of generally U-shaped cross section having proximal and distal ends and having an open-sided channel therein for slidably receiving one of said jaws, stop means provided by said pad adjacent said distal end for limiting the longitudinal insertion of said jaw into said channel from the proximal end thereof, retention means provided by said member adjacent said proximal end and completely spanning said channel at its proximal end for preventing complete transverse movement of said jaw out of said channel, and latching means for securing said jaw against longitudinal displacement from said channel, said latching means including operatively associated male and female elements provided by said jaw and pad intermediate the length thereof and normally disposed in a latching position but shiftable into a releasing position when an intermediate portion of said channel-defining member is flexed to bow away from said jaw to separate said male and female elements.

12. The structure of claim 1 in which said male element is provided by said pad and said female element by said jaw.

13. The structure of claim 11 in which said retention means is a bridge member formed integrally with said pad and completely spanning said channel at said proximal end.

* * * * *